United States Patent [19]

Coffey

[11] Patent Number: 5,076,262

[45] Date of Patent: Dec. 31, 1991

[54] EAR FLATTENING DEVICE

[76] Inventor: Brian M. Coffey, 8931 SE. Cora St., Portland, Oreg. 97266

[21] Appl. No.: 657,242

[22] Filed: Feb. 14, 1991

Related U.S. Application Data

[63] Continuation of Ser. No. 442,969, Nov. 29, 1989, abandoned.

[51] Int. Cl.$^5$ ............................................. A61F 5/08
[52] U.S. Cl. ................................... 128/76 R; 128/866
[58] Field of Search ..................... 128/76 R, 866, 857, 128/864, 163

[56] References Cited

U.S. PATENT DOCUMENTS

| | | | |
|---|---|---|---|
| 543,455 | 7/1895 | Weber | 128/76 R |
| 1,050,744 | 1/1913 | Monier-Williams | 128/76 R |
| 1,826,309 | 10/1931 | Gaston et al. | 2/174 |
| 2,633,127 | 3/1953 | Scholl | 128/894 |

FOREIGN PATENT DOCUMENTS

| | | | |
|---|---|---|---|
| 240649 | 6/1911 | Fed. Rep. of Germany | 128/76 R |
| 727602 | 6/1932 | France | 128/76 R |
| 13498 | of 1897 | United Kingdom | 128/893 |
| 25712 | of 1904 | United Kingdom | 128/76 R |

Primary Examiner—V. Millin
Assistant Examiner—Linda C. M. Dvorak
Attorney, Agent, or Firm—Olson & Olson

[57] ABSTRACT

An ear flattening device is provided by a pair of flexible pads interconnected by a flexible, one-piece spacer block. The outer sides of the pads are provided with a layer of pressure sensitive adhesive for releasably bonding the pads one to the back side of the ear and the other to the confronting surface of the head. The adhesive layers are protected temporarily by a removable cover sheet. In one embodiment a single spacer block is substantially centered within the perimeter of the pair of pads, and in a second embodiment the pads are elongated arcuately and two laterally spaced apart spacer blocks are positioned approximately in the center of the lateral halves of the pads. In both instances the central positioning of the spacer blocks centralizes the pull on the pads relative to the skin and thereby maximizes the adherence of the pads to the skin.

8 Claims, 1 Drawing Sheet

EAR FLATTENING DEVICE

This application is a continuation, of application Ser. No. 442,969, filed Nov. 29, 1989, now abandoned.

BACKGROUND OF THE INVENTION

This invention relates to cosmetic devices, and more particularly to a device for drawing the ears closer to the head, for cosmetic enhancement.

Public figures, such as artists, actors, speakers, models and others, whose ears protrude significantly from the face, attempt a wide variety of corrective techniques in an effort to enhance their appearance. These techniques range from costly cosmetic surgery to the use of wads of adhesive tape interposed between the ears and head.

Cosmetic surgery is more costly than most people can afford, and the lack of reliability of adhesion renders the use of wads of adhesive tape unsatisfactory. Intermediate those extremes is the use of ornamental or corrective devices which are attached to the outwardly exposed portions of the ears. Exemplary of these types of devices are those disclosed in U.S. Pat. Nos. 516,135; 543,455; 1,062,654; 1,338,090: 2,339,572; 2,896,613; 3,154,071; 3,238,938; 3,695,256 and 4,187,838. All of these involve the use of mechanical components which are located on the ears in full view, and thus draw attention to an unnatural appearance.

U.S. Pat. No. 1,050,744 discloses a device for the prevention and correction of protruding ears, which comprises a pair of discs secured together by thread and having adhesive on their outer surfaces for securing one of the discs to the back surface of the ear and the other disc to the confronting surface of the face, the length of the thread determining the degree to which the ear is spaced outwardly from the face. Manufacture of this device is quite costly since the incorporation of threads of various length requires excessive manual labor while limiting production volume.

SUMMARY OF THE INVENTION

In its basic concept, the ear flattening device of this invention comprises a pair of flexible pads interconnected by a flexible, one-piece spacer block, the pads being provided with an adhesive layer on their outer surfaces for releasable attachment one to the back surface of an ear and the other to the confronting surface of the head.

It is by virtue of the foregoing basic concept that the principal objective of this invention is achieved; namely, to provide an ear flattening device of the class described which overcomes the aforementioned limitations and disadvantages of prior devices and techniques.

Another objective of this invention is the provision of an economical ear flattening device of the class described which secures the ear reliably but releasably in attractively flattened condition.

A further objective of this invention is to provide an economical ear flattening device of the class described which is concealed behind the ear and thus presents the ear to view in a normal and attractive manner.

A still further objective of this invention is the provision of an economical ear flattening device of the class described which is capable of flattening the ears to different degrees, whereby to provide maximum attractiveness of the ears of different persons.

Still another objective of this invention is to provide an ear flattening device of the class described which is of simplified construction for economical and high volume manufacture, rendering the device expendable.

The foregoing and other objects and advantages of this invention will appear from the following detailed description, taken in connection with the accompanying drawings of preferred embodiments.

DESCRIPTION OF THE PREFERRED EMBODIMENT

Figure 1:
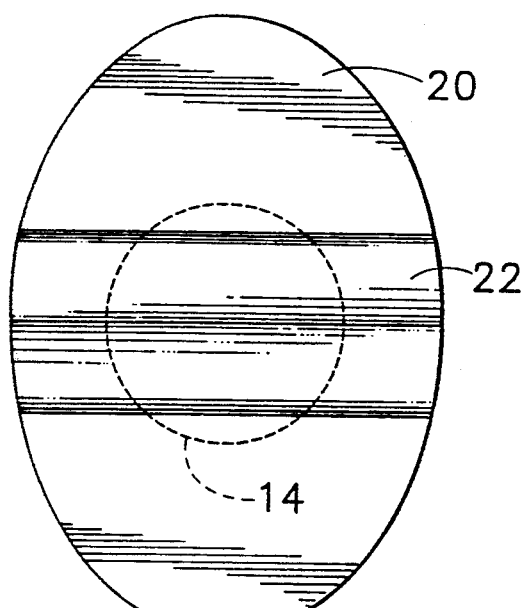
FIG. 1 is an enlarged plan view of an ear flattening device embodying the features of this invention.
Figure 2:
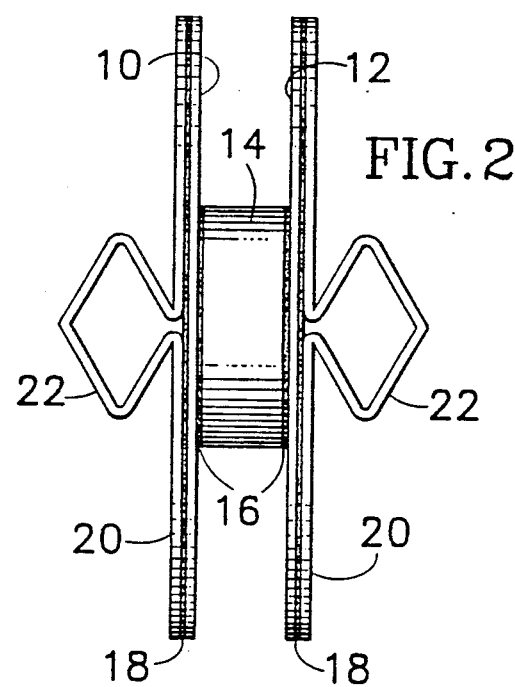
FIG. 2 is a side elevation as viewed from the right or left of FIG. 1.
Figure 3:
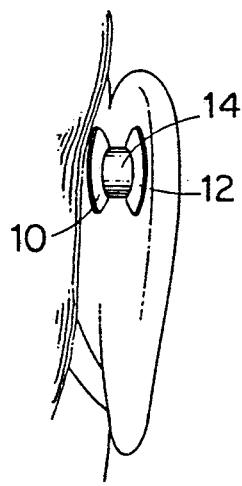
FIG. 3 is a fragmentary rear elevation of portions of a person's head and ear showing the ear flattening device of FIGS. 1 and 2 installed in operative, ear flattening position.

Referring first to the embodiment illustrated in FIGS. 1-3 of the drawings, the ear flattening device illustrated includes a pair of pads 10 and 12 in the preferred form of thin, flexible sheets. Although the sheets may be made of any suitable flexible material, such as cloth, rubber, or synthetic thermoplastic resin, they preferably are formed of medical grade adhesive tape.

The pads 10 and 12 are joined together in spaced apart relationship by a flexible, one-piece block 14 of sponge rubber, foamed synthetic resin, or other elastomeric material of suitable flexibility and compressibility. The opposite surfaces of the block 14 are provided with a layer of adhesive 16 by which to secure said surfaces to the inner surfaces of the pads 10 and 12.

Each pad is provided with a layer 18 of pressure sensitive adhesive on its outer side. The adhesive layer is covered temporarily with a removable cover sheet 20 to protect the adhesive layer prior to use.

The cover sheet illustrated is provided as a single sheet of paper or other suitable material folded at its center to form an outwardly projecting, diamond-shaped pull tab 22. The diamond shape allows the pull tab to collapse against the cover sheet 22 to minimum thickness for convenient packaging and storage. However, when the pull tab is grasped between thumb and finger, it collapses inwardly to form an elongated, laterally extending pull tab of sufficient gripping surface area to enable pulling the cover sheet 20 away from the adhesive layer 18.

Referring now primarily to FIG. 3 of the drawings, the ear flattening device described hereinbefore is applied by first removing the protective cover sheets 20 to expose the pressure sensitive adhesive layers 18 on the outer sides of the sheet pads 10 and 12. The interconnected pads then are positioned behind the ear of the wearer and the ear pressed inwardly toward the head. The adhesive layers 18 thus are brought into pressure contact with the back side of the ear and the confronting side of the head. When inward pressing of the ear is relieved, the ear retracts laterally outward from the side of the head to the extent permitted by the thickness of the block 14 interposed between the pads.

The thickness of the block 14 extending between the pads 10 and 12 may be varied to provide the degree of flattening of the ear that is found to be the most attractive for a given wearer.

Figure 4:
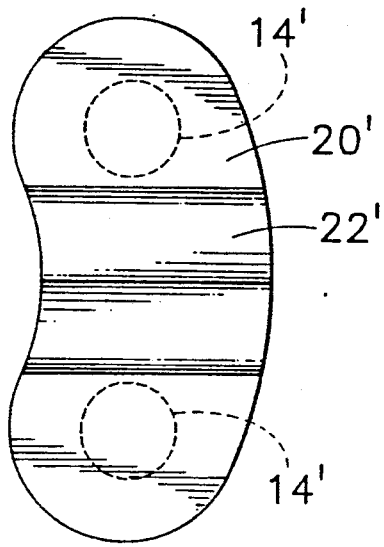
FIG. 4 is a plan view of a second embodiment of ear flattening device of this invention.
Figure 5:
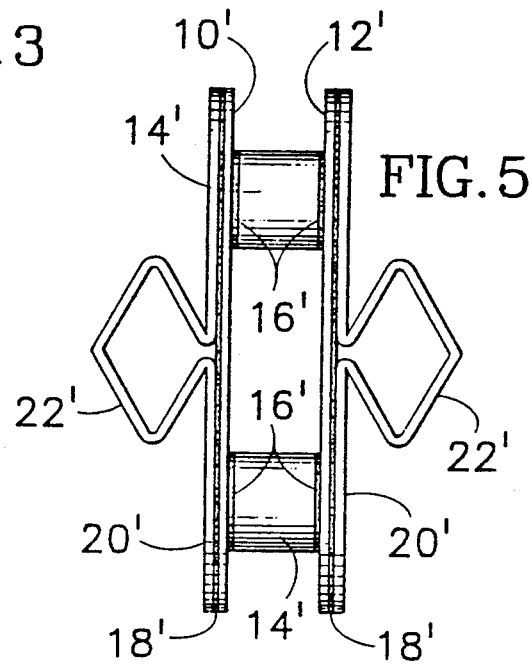
FIG. 5 is a side elevation as viewed from the right of FIG. 4.

FIG. 4 illustrates a modified form of ear flattening device embodying the features of this invention. In this modification, the same assembly of sheet pads 10' and 12' and connecting blocks 14' is employed as in the previously described embodiment. In this modification, however, the plan view shape is elongated arcuately, rather than elliptical as in the previous form. Two laterally spaced apart spacer blocks 14' are provided inwardly of the opposite ends, approximately in the center of the lateral halves of the pads. This form is utilized advantageously to flatten ears that are considerably larger in size than those with which the first described embodiment is used.

It is to be noted that the spacer block 14 is substantially centered within the perimeter of the sheet pads 10 and 12 of the embodiment shown in FIGS. 1-3 and that the pair of spacer blocks 14' of the FIG. 4 embodiment are substantially centered within the lateral halves of the sheet pads 10' and 12'. This central positioning of the blocks centralizes the pull on the sheet pads relative to the skin and therefore maximizes the adherence of the sheet pads to the skin. This ensures against premature or unintended release of the device from the operative, ear flattening position.

It will be apparent to those skilled in the art that various changes may be made in the size, shape, type, number and arrangement of parts of the ear flattening device described hereinbefore, without departing from the spirit of this invention and the scope of the appended claims.

I claim:

1. An ear flattening device, comprising:
   a) a pair of flexible pads having inner and outer sides,
   b) a flexible, one-piece spacer block of predetermined thickness secured to the inner sides of and interconnecting the pair of pads, and
   c) a layer of pressure sensitive adhesive on the outer sides of the pair of pads for releasably securing the pads one to the back side of an ear and the other to the confronting surface of the head, the thickness of the spacer block being selected to flatten the ear to a predetermined extent.

2. The ear flattening device of claim 1 wherein the spacer block is of foamed elastomer.

3. The ear flattening device of claim 1 wherein the spacer block interconnects the pair of pads at substantially the center portion of the pad.

4. The ear flattening device of claim 1 wherein the pair of pads are elongated arcuately and a pair of spaced apart spacer blocks interconnect the pads at substantially the center portion of the lateral halves of the pads.

5. The ear flattening device of claim 1 including a protective cover sheet secured removably to the outer surface of each layer of pressure sensitive adhesive for protecting said layer prior to use, and pull tab means on the outer side of each cover sheet and extending outwardly therefrom for grasping between fingers of a hand for removing the cover sheet from the underlying layer of pressure sensitive adhesive.

6. The ear flattening device of claim 5 wherein each cover sheet and associated pull tab means comprises a single piece of sheet material folded at its center to form a diamond-shaped pull tab projecting outwardly from the central portion of the cover sheet.

7. The ear flattening device of claim 4 including a protective cover sheet secured removably to the outer surface of each layer of pressure sensitive adhesive for protecting said layer prior to use, and pull tab means on the outer side of each cover sheet and extending outwardly therefrom for grasping between fingers of a hand for removing the cover sheet from the underlying layer of pressure sensitive adhesive.

8. The ear flattening device of claim 7 wherein each cover sheet and associated pull tab means comprises a single piece of sheet material folded at its center to form a diamond-shaped pull tab projecting outwardly from the central portion of the cover sheet.

* * * * *